US009029094B2

(12) United States Patent
Moreau et al.

(10) Patent No.: US 9,029,094 B2
(45) Date of Patent: May 12, 2015

(54) BIOMECHANICAL-BASED METHODS OF DIAGNOSING SCOLIOSIS

(75) Inventors: Alain Moreau, Montreal (CA);
Guoruey Wong, Montreal (CA)

(73) Assignee: Chu Sainte-Justine, Montreal (CA)

( * ) Notice: Subject to any disclaimer, the term of this patent is extended or adjusted under 35 U.S.C. 154(b) by 0 days.

(21) Appl. No.: 13/822,982

(22) PCT Filed: Oct. 4, 2011

(86) PCT No.: PCT/CA2011/050625
§ 371 (c)(1),
(2), (4) Date: Mar. 13, 2013

(87) PCT Pub. No.: WO2012/045176
PCT Pub. Date: Apr. 12, 2012

(65) Prior Publication Data
US 2013/0183695 A1    Jul. 18, 2013

Related U.S. Application Data

(60) Provisional application No. 61/389,348, filed on Oct. 4, 2010.

(51) Int. Cl.
*G01N 33/53* (2006.01)
*G01N 33/00* (2006.01)
*G01N 33/68* (2006.01)
*A61B 5/00* (2006.01)

(52) U.S. Cl.
CPC ........ *G01N 33/6893* (2013.01); *G01N 33/6863* (2013.01); *G01N 2800/10* (2013.01); *A61B 5/4566* (2013.01)

(58) Field of Classification Search
None
See application file for complete search history.

(56) References Cited

U.S. PATENT DOCUMENTS

| 6,025,155 | A | 2/2000 | Hadlaczky et al. |
| 6,077,677 | A | 6/2000 | Hodgson et al. |
| 6,204,023 | B1 | 3/2001 | Robinson et al. |
| 6,905,456 | B1 | 6/2005 | Brunner et al. |
| 6,916,298 | B2 | 7/2005 | VanBrunt et al. |
| 2002/0160970 | A1 | 10/2002 | Hadlaczky et al. |
| 2003/0083293 | A1 | 5/2003 | Hadlaczky et al. |
| 2005/0130250 | A1 | 6/2005 | Moreau |
| 2008/0255477 | A1* | 10/2008 | Woggon et al. ............... 600/595 |
| 2009/0177127 | A1 | 7/2009 | Sherman et al. |
| 2009/0287100 | A1 | 11/2009 | Aranciva |
| 2010/0173296 | A1* | 7/2010 | Moreau ............................. 435/6 |

FOREIGN PATENT DOCUMENTS

| WO | 2006/068459 | 6/2006 | |
| WO | WO 2006068459 A1 | * 6/2006 | |
| WO | 2008/119170 | 10/2008 | |
| WO | WO 2008119170 A1 | * 10/2008 | ........... G01N 33/543 |

OTHER PUBLICATIONS

Bast et al., Translational Crossroads for Biomarkers, Clin Cancer Res 2005; 11(17), 6103-6108.*
LaBaer et al., So you want to look for biomarkers, Journal of Proteome Research 2005; 4, 1053-1059.*
Baker, In Biomarkers We Trust, Nature Biotechnology 2005; 23(3) 297-304.*
Cuff. The American Heritage Medical Dictionary. Boston: Houghton Mifflin, 2007. Credo Reference. Web. Apr. 23, 2014.*
Axenovich et al. "Segregation analysis of idiopathic scoliosis: demonstration of a major gene effect", (1999), Am J Med Genet; vol. 86(4): 389-394.
Bagnall KM et al., "The International Research Society of Spinal Deformities (IRSSD) and its contribution to science" (2009), Scoliosis; 4(28): 1-15.
Blank RD et al., "A genomic approach to scoliosis pathogenesis", (1999), Lupus; 8(5): 356-360.
Colwell et al., "Thrombosis Prevention After Total Hip Arthroplasty", (2010), J Bone Joint Surg Am; 92(3): 527-535.
Denhardt et al., "Osteopontin as a means to cope with environmental insults: regulation of inflammation, tissue remodelling, and cell survival", (2001), The Journal of Clinical Investigation; 107(9): 1055-1061.
Galili et al., "A novel intermittent mechanical compression device for stasis prevention in the lower limbs during limited mobility situations", (2007), Thromb Res; 121(1): 37-41. Epub Apr. 17, 2007.
Goldberg MS et al., "The Ste-Justine Adolescent Idiopathic Scoliosis Cohort Study. Part I: Description of the study" (1994), Spine; 19:1551-1561.
Harlow et al., (1988), Antibody: A Laboratory Manual, Chapter Generating Monoclonal Antibodies, CSH Laboratories: 203-221.
Hyatt BA et al., "Initiation of vertebrate left-right axis formation by maternal Vg1", (1996), Nature; 384(6604): 62-65.
Kohler et al., "Continuous cultures of fused cells secreting antibody ofpredefined specificity"(1975), Nature; 256:495.
Lindenbaum et al., "A mammalian artificial chromosome engineering system (ACE System) applicable to biopharmaceutical protein production, transgenesis and gene-based cell therapy" (2004), Nucleic Acids Research; 32(21):e172.
Machida M, "Cause of Idiopathic Scoliosis", (1999), Spine; vol. 24(24), 2576-2583.
Moreau et al., "High circulating levels of osteopontin are associated with idiopathic scoliosis onset and spinal deformity progression", SRS 44th Annual meeting and Course, Paper #79, Sep. 2009.
Poitras B et al., "The Ste-Justine Adolescent Idiopathic Scoliosis Cohort Study. Part IV: surgical correction and back pain" (1994), Spine; 19: 1582-1588.
Roth JA et al., "Melatonin Promotes Osteoblast Differentiation and Bone Formation", (1999), The Journal of Biological Chemistry; 274(31): 22041-22047.

(Continued)

*Primary Examiner* — Galina Yakovleva
*Assistant Examiner* — Andrea S Grossman
(74) *Attorney, Agent, or Firm* — Goudreau Gage Dubuc; Julie Gauvreau

(57) ABSTRACT

Methods for diagnosing a scoliosis (e.g., adolescent idiopathic scoliosis (AIS)) and/or a predisposition to developing a scoliosis based on the determination of the variation of osteopontin (OPN) levels induced by mechanical forces/stimuli are described.

24 Claims, 7 Drawing Sheets

(56) References Cited

OTHER PUBLICATIONS

Von Gall C et al., " Transcription factor dynamics and neuroendocrine signalling in the mouse pineal gland: a comparative analysis of melatonin-deficient C57BL mice and melatonin-proficient C3H mice", (2000), Eur J Neurosci; 12(3): 964-972.

Weinstein SL et al., "Adolescent idiopathic scoliosis" (2008), Lancet; 371: 1527-1537.

Weiss HR et al., "Rate of complications in scoliosis surgery—a systematic review of the Pub Med literature" (2008), Scoliosis; 3(9): 1-18.

Wise CA et al., "Localization of Susceptibility to Familial Idiopathic Scoliosis" (2000), Spine; 25(18): 2372-2380.

Wong G, "Étude de la mécanotransduction dans la scoliose idiopathique de l'adolescence (SIA)" (2011), Mémoire de Maîtrise, Faculté de médecine, Université de Montréal: 1-103.

International Search Report and Written Opinion mailed Jan. 3, 2012 in PCT/CA2011/050625 to Moreau et al.

International Preliminary Examination Report mailed Apr. 18, 2013 in PCT/CA2011/050625 to Moreau et al.

Supplementary European Search Report mailed Dec. 20, 2013 in EP11830173.8 to Moreau et al.

Moreau A et al., "Pediatric scoliosis predictive blood tests: progress and challenges for clinicians" (2010), Scoliosis; 5 (Suppl 1): 03.

Terai K et al., "Role of Osteopontin in Bone Remodeling Caused by Mechanical Stress" (1999), Journal of Bone and Mineral Research; 14(6): 839-849.

Vetrone SA et al., "osteopontin promotes fibrosis in dystrophic mouse muscle by modulating immune cell subsets and intramuscular TGF-beta" (2009), The Journal of Clinical Investigation; 119(6): 1583-1594.

Bast et al., "Translational Crossroads for Biomarkers" (2005), Clin Cancer Res; 11(17): 6103-6108.

Labaer et al., "So, You Want to Look for Biomarkers" (2005),Journal of Proteome Research; 4: 1053-1059.

Baker, "In Biomarkers We Trust" (2005), Nature Biotechnology; 23(3): 297-304.

Cuff, The American Heritage Medical Dictionary. Boston: Houghton Mifflin, 2007. Credo Reference. Web Apr. 23, 2014.

Garrett SH et al., "Short and long term gene expression variation and networking in human proximal tubule cells when exposed to cadmium" (2013), BMC Medical Genomics; 6(Suppl 1): 82.

\* cited by examiner

Mechanical stimulation

NM_001040058 transcript variant 1
```
   1 ctccctgtgt tggtggagga tgtctgcagc agcatttaaa ttctgggagg gcttggttgt
  61 cagcagcagc aggaggaggc agagcacagc atcgtcggga ccagactcgt ctcaggccag
 121 ttgcagcctt ctcagccaaa cgccgaccaa ggaaaactca ctaccatgag aattgcagtg
 181 atttgctttt gcctcctagg catcacctgt gccataccag ttaaacaggc tgattctgga
 241 agttctgagg aaaagcagct ttacaacaaa tacccagatg ctgtggccac atggctaaac
 301 cctgacccat ctcagaagca gaatctccta gccccacaga atgctgtgtc ctctgaagaa
 361 accaatgact ttaaacaaga gacccttcca agtaagtcca acgaaagcca tgaccacatg
 421 gatgatatgg atgatgaaga tgatgatgac catgtggaca gccaggactc cattgactcg
 481 aacgactctg atgatgtaga tgacactgat gattctcacc agtctgatga gtctcaccat
 541 tctgatgaat ctgatgaact ggtcactgat tttcccacgg acctgccagc aaccgaagtt
 601 ttcactccag ttgtccccac agtagacaca tatgatggcc gaggtgatag tgtggtttat
 661 ggactgaggt caaaatctaa gaagttcgc agacctgaca tccagtaccc tgatgctaca
 721 gacgaggaca tcacctcaca catggaaagc gaggagttga atggtgcata caaggccatc
 781 cccgttgccc aggacctgaa cgcgccttct gattgggaca ccgtgggaa ggacagttat
 841 gaaacgagtc acctggatga ccagagtgct gaaacccaca gccacaagca gtccagatta
 901 tataagcgga aagccaatga tgagagcaat gagcattccg atgtgattga tagtcaggaa
 961 cttttccaaag tcagccgtga attccacagc catcaatttc acagccatga agatatgctg
1021 gttgtagacc ccaaagtaa ggaagaagat aaacacctga atttcgtat ttctcatgaa
1081 ttagatagtg catcttctga ggtcaattaa aagcagaaaa aatacaattt ctcactttgc
1141 atttagtcaa aagaaaaaat gctttatagc aaaatgaaag agaacatgaa atgcttcttt
1201 ctcagtttat tggttgaatg tgtatctatt tgagtctgga ataactaat gtgtttgata
1261 attagtttag tttgtggctt catggaaact ccctgtaaac taaaagcttc agggttatgt
1321 ctatgttcat tctatagaag aaatgcaaac tatcactgta ttttaatatt tgttattctc
1381 tcatgaatag aaatttatgt agaagcaaac aaaatacttt acccactta aaaagagaat
1441 ataacatttt atgtcactat aatcttttgt tttttaagtt agtgtatatt tgttgtgat
1501 tatctttttg tggtgtgaat aaatctttta tcttgaatgt aataagaatt tggtggtgtc
1561 aattgcttat ttgttttccc acggttgtcc agcaattaat aaaacataac ctttttact
1621 gcctaaaaaa aaaaaaaaa a
```

NM_000582 transcript variant 2
```
   1 ctccctgtgt tggtggagga tgtctgcagc agcatttaaa ttctgggagg gcttggttgt
  61 cagcagcagc aggaggaggc agagcacagc atcgtcggga ccagactcgt ctcaggccag
 121 ttgcagcctt ctcagccaaa cgccgaccaa ggaaaactca ctaccatgag aattgcagtg
 181 atttgctttt gcctcctagg catcacctgt gccataccag ttaaacaggc tgattctgga
 241 agttctgagg aaaagcagct ttacaacaaa tacccagatg ctgtggccac atggctaaac
 301 cctgacccat ctcagaagca gaatctccta gccccacaga ccccttccaag taagtccaac
 361 gaaagccatg accacatgga tgatatggat gatgaagatg atgatgacca tgtggacagc
 421 caggactcca ttgactcgaa cgactctgat gatgtagatg acactgatga ttctcaccag
 481 tctgatgagt ctcaccattc tgatgaatct gatgaactgg tcactgattt tcccacggac
 541 ctgccagcaa ccgaagtttt cactccagtt gtccccacag tagacacata tgatggccga
 601 ggtgatagtg tggtttatgg actgaggtca aaatctaaga gtttcgcag acctgacatc
 661 cagtaccctg atgctacaga cgaggacatc acctcacaca tggaaagcga ggagttgaat
 721 ggtgcataca aggccatccc cgttgcccag gacctgaacg cgccttctga ttgggacacc
 781 gtgggaaga acagttatga aacgagtcag ctggatgacc agagtgctga acccacagc
 841 cacaagcagt ccagattata taagcggaaa gccaatgatg agagcaatga gcattccgat
 901 gtgattgata gtcaggaact tccaaagtc agccgtgaat tccacagcca tgaatttcac
 961 agccatgaag atatgctggt tgtagacccc aaagtaagg aagaagataa acacctgaaa
1021 tttcgtattt ctcatgaatt agatagtgca tcttctgagg tcaattaaaa ggagaaaaaa
1081 tacaatttct cactttgcat ttagtcaaaa gaaaaaatgc tttatagcaa aatgaaagag
1141 aacatgaaat gcttctttct cagtttattg gttgaatgtg tatctatttg agtctggaa
1201 taactaatgt gtttgataat tagtttagtt tgtggcttca tggaaactcc ctgtaaacta
1261 aaagcttcag ggttatgtct atgttcattc tatagaagaa atgcaaacta tcactgtatt
1321 ttaatatttg ttattctctc atgaatagaa atttatgtag aagcaaacaa aatactttta
1381 cccacttaaa aagagaatat aacattttat gtcactataa tcttttgttt ttaagttag
1441 tgtatatttt gttgtgatta tctttttgtg gtgtgaataa atctttatc ttgaatgtaa
1501 taagaatttg gtggtgtcaa ttgcttattt gttttcccac ggttgtccag caattaataa
1561 aacataacct tttttactgc ctaaaaaaaa aaaaaaaaaa aaaaaaaaaa aaaaa
```

FIG. 6

NM_001040060 transcript variant 3

```
   1 ctccctgtgt tggtggagga tgtctgcagc agcatttaaa ttctgggagg gcttggttgt
  61 cagcagcagc aggaggaggc agagcacagc atcgtcggga ccagactcgt ctcaggccag
 121 ttgcagcctt ctcagccaaa cgccgaccaa ggaaaactca ctaccatgag aattgcagtg
 181 atttgctttt gcctcctagg catcacctgt gccataccag ttaaacaggc tgattctgga
 241 agttctgagg aaaagcagaa tgctgtgtcc tctgaagaaa ccaatgactt taaacaagag
 301 acccttccaa gtaagtccaa cgaaagccat gaccacatgg atgatatgga tgatgaagat
 361 gatgatgacc atgtggacag ccaggactcc attgactcga acgactctga tgatgtagat
 421 gacactgatg attctcacca gtctgatgag tctcaccatt ctgatgaatc tgatgaactg
 481 gtcactgatt ttcccacgga cctgccagca accgaagttt tcactccagt tgtccccaca
 541 gtagacacat atgatggccg aggtgatagt gtggtttatg gactgaggtc aaaatctaag
 601 aagtttcgca gacctgacat ccagtaccct gatgctacag acgaggacat cacctcacac
 661 atggaaagcg aggagttgaa tggtgcatac aaggccatcc ccgttgccca ggacctgaac
 721 gcgccttctg attgggacag ccgtgggaag gacagttatg aaacgagtca gctggatgac
 781 cagagtgctg aaacccacag ccacaagcag tccagattat ataagcggaa agccaatgat
 841 gagagcaatg agcattccga tgtgattgat agtcaggaac tttccaaagt cagccgtgaa
 901 ttccacagcc atgaatttca gccatgaaga tatgctgg ttgtagaccc caaaagtaag
 961 gaagaagata acacctgaa atttcgtatt tctcatgaat tagatagtgc atcttctgag
1021 gtcaattaaa aggagaaaaa atacaatttc tcactttgca tttagtcaaa agaaaaaatg
1081 ctttatagca aatgaaaga gaacatgaaa tgcttctttc tcagtttatt ggttgaatgt
1141 gtatctattt gagtctggaa ataactaatg tgtttgataa ttagtttagt ttgtggcttc
1201 atggaaactc cctgtaaact aaaagcttca gggttatgtc tatgttcatt ctatagaaga
1261 aatgcaaact atcactgtat tttaatattt gttattctct catgaataga aatttatgta
1321 gaagcaaaca aatacttttt acccacttaa aagagaata taacatttta tgtcactata
1381 atcttttgtt ttttaagtta gtgtatattt tgttgtgatt atcttttttgt ggtgtgaata
1441 aatcttttat cttgaatgta ataagaattt ggtggtgtca attgcttatt tgttttccca
1501 cggttgtcca gcaattaata aaacataacc ttttttactg cctaaaaaaa aaaaaaaaaa
```

NP_001035147 isoform a
```
  1 mriavicfcl lgitcaipvk qadsgsseek qlynkypdav atwlnpdpsq kqnllapqna
 61 vsseetndfk qetlpsksne shdhmddmdd edddhvdsq dsidsndsdd vddtddshqs
121 deshhsdesd elvtdfptdl patevftpvv ptvdtydgrg dsvvyglrsk skkfrrpdiq
181 ypdatdedit shmeseelng aykaipvaqd lnapsdwdsr gkdsyetsql ddqsaethsh
241 kqsrlykrka ndesnehsdv idsqelskvs refhshefhs hedmlvvdpk skeedkhlkf
301 risheldsas sevn
```

NP_000573 isoform b
```
  1 mriavicfcl lgitcaipvk qadsgsseek qlynkypdav atwlnpdpsq kqnllapqtl
 61 psksneshdh mddmddeddd dhvdsqdsid sndsddvddt ddshqsdesh hsdesdelvt
121 dfptdlpate vftpvvptvd tydgrgdsvv yglrskskkf rrpdiqypda tdeditshme
181 seelngayka ipvaqdlnap sdwdsrgkds yetsqlddqs aethshkqsr lykrkandes
241 nehsdvidsq elskvsrefh shefhshedm lvvdpkskee dkhlkfrish eldsassevn
```

NP_001035149 isoform c
```
  1 mriavicfcl lgitcaipvk qadsgsseek qnavsseetn dfkqetlpsk sneshdhmdd
 61 mddedddhv dsqdsidsnd sddvddtdds hqsdeshhsd esdelvtdfp tdlpatevft
121 pvvptvdtyd grgdsvvygl rskskkfrrp diqypdatde ditshmesee lngaykaipv
181 aqdlnapsdw dsrgkdsyet sqlddqsaet hshkqsrlyk rkandesneh sdvidsqels
241 kvsrefhshe fhshedmlvv dpkskeedkh lkfrisheld sassevn
```

FIG. 6 (continued)

BIOMECHANICAL-BASED METHODS OF DIAGNOSING SCOLIOSIS

CROSS-REFERENCE TO RELATED APPLICATIONS

This application is a National Entry Application of PCT application no PCT/CA2011/050625 filed on Oct. 4, 2011 and published in English under PCT Article 21(2), which itself claims benefit of U.S. provisional application Ser. No. 61/389,348, filed on Oct. 4, 2010. All documents above are incorporated herein in their entirety by reference.

STATEMENT REGARDING FEDERALLY SPONSORED RESEARCH OR DEVELOPMENT

N/A.

FIELD OF THE INVENTION

The present invention relates to the diagnosis of a predisposition to developing a scoliosis (e.g., adolescent idiopathic scoliosis (AIS)) and to screening assays for identifying compounds for treating scoliosis.

REFERENCE TO SEQUENCE LISTING

Pursuant to 37 C.F.R. 1.821(c), a sequence listing is submitted herewith as an ASCII compliant text file named 765 USPTO-sequence listing as filed_ST25, created on Mar. 13, 2013 and having a size of 15 Kb kilobytes. The content of the aforementioned file is hereby incorporated by reference in its entirety.

BACKGROUND OF THE INVENTION

Scoliosis is a medical condition in which a person's spine is curved from side to side, and may also be rotated. It is an abnormal lateral curvature of the spine. On an x-ray, the spine of an individual with a typical scoliosis may look more like an "S" or a "C" than a straight line.

Spinal deformities and scoliosis in particular represent the most prevalent type of orthopedic deformities in children and adolescents, while idiopathic scoliosis (IS) represents the most common form of scoliosis. The etiology of adolescent idiopathic scoliosis (AIS) is unclear. AIS affects mainly girls in number and severity but in spite of several studies suggesting a genetic predisposition, the form of inheritance remains uncertain (Axenovich T I et al., *Am J Med Genet* 1999, 86(4): 389-394; Wise C A et al., *Spine* 2000, 25(18): 2372-2380; Blank R D et al., *Lupus* 1999, 8(5): 356-360; Giampietro P F et al., *Am J Med Genet* 1999, 83(3):164-177). Several divergent perspectives have been postulated to better define this etiology (Machida M., *Spine* 1999, 24(24): 2576-2583; Roth J A et al., *J Biol Chem* 1999, 274(31): 22041-22047; Hyatt B A et al., *Nature* 1996, 384(6604): 62-65; von Gall C et al., *Eur J Neurosci* 2000, 12(3): 964-972). Genetics, growth hormone secretion, connective tissue structure, muscle structure, vestibular dysfunction, melatonin secretion, and platelet microstructure are major areas of focus. The current opinion is that there is a defect of central control or processing by the central nervous system (CNS) that affects a growing spine and that the spine's susceptibility to deformation varies from one individual to another.

There is unfortunately no method approved by the FDA yet to identify children or adolescents at risk of developing IS to predict which affected individuals require treatment to prevent or stop progression of the disease (Weinstein S L, Dolan L A, Cheng J C et al. Adolescent idiopathic scoliosis. *Lancet* 2008; 371:1527-37). Consequently, the application of current treatments, such as bracing or surgical correction, is delayed until the detection of a significant deformity or a demonstration of clear progression, resulting in a delayed and less-than-optimal treatment (Society S R. Morbidity & Mortality Committee annual Report 2002-2003). Among patients with IS requiring treatment, 80 to 90% will be treated by bracing and around 1% will need surgery to correct the deformity by spinal instrumentation and fusion of the thoracic and/or lumbar spine with the risk of having complications (Weiss H R, Goodall D. Rate of complications in scoliosis surgery—a systematic review of the Pub Med literature. *Scoliosis*. 2008; 3:9). Today in the United States there are approximately one million children between ages 10 and 16 with some degree of IS. One out of every six children diagnosed with scoliosis will have a curve that progresses to a degree that requires active treatment. About 29,000 scoliosis surgeries are performed every year in North America, resulting in significant psychological and physical morbidity (Goldberg M S, Mayo N E, Poitras B et al. The Ste-Justine Adolescent Idiopathic Scoliosis Cohort Study. Part I: Description of the study. *Spine* 1994; 19:1551-61; Poitras B, Mayo N E, Goldberg M S et al. The Ste-Justine Adolescent Idiopathic Scoliosis Cohort Study. Part IV: Surgical correction and back pain. *Spine* 1994; 19:1582-8).

There is a need for methods for diagnosing diseases involving spinal deformities (e.g., scoliosis, such as AIS), for diagnosing a predisposition to scoliosis and for identifying compounds for preventing or treating these diseases.

The present description refers to a number of documents, the content of which is herein incorporated by reference in their entirety.

SUMMARY OF THE INVENTION

The present inventors have demonstrated that the changes in the levels of osteopontin (OPN) (also called secreted phosphoprotein 1, bone sialoprotein I, early T-lymphocyte activation 1) induced by bodily-applied mechanical force are more pronounced in control subjects relative to scoliotic patients (e.g., surgical case patients (Cobb angle$\geq 45°$)).

More specifically, in accordance with the present invention, there is provided a method (e.g., an in vitro method) for diagnosing a scoliosis and/or a predisposition to developing a scoliosis (e.g., an Idiopathic Scoliosis (IS) such as Infantile Idiopathic Scoliosis, Juvenile Idiopathic Scoliosis or Adolescent Idiopathic Scoliosis (AIS)) in a subject comprising: (a) measuring a first level of osteopontin (OPN) in a biological sample from said subject; (b) applying a mechanical stimulus or force to one or more members from said subject; (c) measuring a second level of OPN in a corresponding biological sample from said subject after the start of the application of said biomechanical stimulus; (d) determining a variation between said first level of OPN and said second level of OPN; (e) comparing said variation to a control variation value; and (f) determining whether said subject has a scoliosis or is predisposed to developing a scoliosis based on said comparison.

In a specific embodiment, the control variation value corresponds to a variation between a first level of OPN and a second level of OPN determined in corresponding biological samples from a subject not having a scoliosis or not a likely candidate for developing scoliosis. In another specific embodiment, a lower variation determined in said subject relative to said control variation value is indicative that said subject has a scoliosis or has a predisposition to developing a scoliosis. In another specific embodiment, said scoliosis is an idiopathic scoliosis. In another specific embodiment, said idiopathic scoliosis is adolescent idiopathic scoliosis (AIS). In another specific embodiment, said biological sample is a biological fluid. In another specific embodiment, said biological fluid is a blood-derived sample. In another specific embodiment, said blood-derived sample is plasma. In another specific embodiment, said one or more members is an arm. In another specific embodiment, said mechanical stimulus or force is a pulsative compressive pressure. In another specific embodiment, said pulsative compressive pressure is applied using an inflatable strap. In another specific embodiment, said pulsative compressive pressure is applied using an inflatable cuff. In another specific embodiment, said mechanical stimulus or force is applied for a period of at least about 15 minutes. In another specific embodiment, said mechanical stimulus or force is applied for a period of between about 30 to about 90 minutes. In another specific embodiment, said mechanical stimulus or force is applied for a period of about 90 minutes. In another specific embodiment, the subject is a likely candidate for developing adolescent idiopathic scoliosis.

In accordance with another aspect of the present invention, there is provided a method (e.g., an in vitro method) for stratifying a subject having a scoliosis (e.g., an Idiopathic Scoliosis (IS) such as Infantile Idiopathic Scoliosis, Juvenile Idiopathic Scoliosis or Adolescent Idiopathic Scoliosis (AIS)), said method comprising: (a) measuring a first level of osteopontin (OPN) in a biological sample from said subject; (b) applying a mechanical stimulus or force to one or more members from said subject; (c) measuring a second level of OPN in a corresponding biological sample from said subject after the start of the application of said biomechanical stimulus; (d) determining a variation between said first level of OPN and said second level of OPN; (e) comparing said variation to a control variation value; and (f) determining whether said subject has a scoliosis or is predisposed to developing a scoliosis based on said comparison.

In accordance with yet another aspect of the present invention, there is provided a kit for diagnosing a scoliosis or a predisposition to developing a scoliosis in a subject, said kit comprising: (a) one or more reagent(s) to determine osteopontin (OPN) levels in a biological sample; and (b) instructions for diagnosing a scoliosis or a predisposition to developing a scoliosis in a subject.

In a specific embodiment, the kit further comprises a device for applying a mechanical stimulus or force on one or more members of the subject. In another specific embodiment, the device is an inflatable strap. In another specific embodiment, the device is an inflatable arm cuff.

In accordance with yet another aspect of the present invention, there is provided an inflatable strap for use in diagnosing a scoliosis or a predisposition to developing a scoliosis in a subject.

In accordance with yet another aspect of the present invention, there is provided a use of an inflatable strap for diagnosing a scoliosis or a predisposition to developing a scoliosis in a human subject.

As used herein the terms "predisposition to developing a scoliosis" refer to a genetic or metabolic predisposition of a subject to develop a scoliosis (i.e. spinal deformity) and/or a more severe scoliosis at a future time.

In an embodiment, the above-mentioned scoliosis is idiopathic scoliosis. In another embodiment, the above-mentioned idiopathic scoliosis is AIS.

In an embodiment, the above-mentioned subject is a mammal, in a further embodiment, a human.

In an embodiment, the above-mentioned subject is a likely candidate for developing a scoliosis, such as idiopathic scoliosis (e.g., Infantile Idiopathic Scoliosis, Juvenile Idiopathic Scoliosis or Adolescent Idiopathic Scoliosis (AIS)). As used herein the terms "likely candidate for developing scoliosis" include subjects (e.g., children) of which at least one parent has a scoliosis (e.g., adolescent idiopathic scoliosis) (e.g., the asymptomatic "at risk" subjects of FIG. 1) and/or having other relative suffering from scoliosis over more than one generation. Among other factors, age (adolescence), gender and other family antecedents are factors that are known to contribute to the risk of developing a scoliosis and are used to a certain degree to assess the risk of developing a scoliosis. In certain subjects, scoliosis develops rapidly over a short period of time to the point of requiring a corrective surgery (often when the deformity reaches a Cobb's angle$\geq 50°$). Current courses of action available from the moment a scoliosis such as AIS is diagnosed (when scoliosis is apparent) include observation (when Cobb's angle is around 10-25°), orthopaedic devices (when Cobb's angle is around 25-30°), and surgery (Cobb's angle over 45°). A more reliable determination of the risk of progression could enable to 1) select an appropriate diet to remove certain food products identified as contributors to scoliosis; 2) select the best therapeutic agent; and/or 3) select the least invasive available treatment such as postural exercises, orthopaedic device, or less invasive surgeries or surgeries without fusions (a surgery that does not fuse vertebra and preserves column mobility). The present invention encompasses selecting the most efficient and least invasive known preventive actions or treatments in view of the determined risk of developing scoliosis.

Any biological sample (e.g., cells, tissues, biological fluids) in which OPN is found may be used in accordance with the methods of the present invention. In an embodiment, the sample is a biological fluid such as urine, saliva, cerebrospinal fluid, or a blood-derived sample such as blood, serum or plasma, which are particularly accessible and provide for a more rapid testing. In a further embodiment, the above-mentioned biological sample is plasma. In an embodiment, the sample is obtained or derived from a subject having an idiopathic scoliosis (e.g., Infantile Idiopathic Scoliosis, Juvenile Idiopathic Scoliosis or Adolescent Idiopathic Scoliosis (AIS)).

In an embodiment, the control variation value is a variation value (corresponding to the difference in OPN levels measured before and after the application of a mechanical stimulus or force) determined in corresponding samples (e.g., a blood-derived sample such as plasma) obtained or derived from a control subject, such as a subject (e.g., age- and/or gender-matched) who has not developed a scoliosis (e.g., idiopathic scoliosis such as Infantile Idiopathic Scoliosis, Juvenile Idiopathic Scoliosis or Adolescent Idiopathic Scoliosis (AIS)), or who is not a likely candidate for developing scoliosis. As used herein the terms "not a likely candidate for developing a scoliosis" refer to the absence in the subject of known factors making him a likely candidate for developing scoliosis (e.g., no family member having scoliosis") In that case, a lower variation in the sample from the subject relative to the corresponding control variation value is indicative that the subject has a scoliosis and/or a predisposition to developing a scoliosis, whereas a higher or substantially identical variation is indicative that the subject does not have a predisposition to developing a scoliosis. In an embodiment, the control variation value is a pre-determined value derived from differences measured using corresponding samples from one or more control subjects (e.g., the mean or median variation calculated from the differences measured using samples from the control subjects).

In an embodiment, the above-mentioned control variation value corresponds to a variation between a first level of OPN and a second level of OPN determined in corresponding biological samples from a subject not having a scoliosis or not a likely candidate for developing scoliosis, and wherein a lower variation determined in said subject relative to said control variation value is indicative that said subject has a scoliosis or has a predisposition to developing a scoliosis.

In another embodiment, the above-mentioned control variation value is a variation value determined in corresponding samples (e.g., a blood-derived sample such as plasma) obtained or derived from a control subject (e.g., age- and/or gender-matched) who has developed a scoliosis with a Cobb angle<45° (e.g., idiopathic scoliosis such as Infantile Idiopathic Scoliosis, Juvenile Idiopathic Scoliosis or Adolescent Idiopathic Scoliosis (AIS)), or who is a likely candidate for developing scoliosis with a Cobb angle<45°. In that case, a lower or a substantially identical variation determined in the samples from the subject relative to the control variation value is indicative that the subject has a scoliosis or a predisposition to developing a scoliosis, whereas a higher variation is indicative that the subject does not have a predisposition to developing a scoliosis with a Cobb angle<45°.

In an embodiment, the control variation value is a predetermined value derived from differences measured using corresponding samples from one or more subjects who have developed a scoliosis with a Cobb angle<45° (e.g., idiopathic scoliosis such as Infantile Idiopathic Scoliosis, Juvenile Idiopathic Scoliosis or Adolescent Idiopathic Scoliosis (AIS)), or who are likely candidates for developing scoliosis with a Cobb angle <45° (e.g., the mean or median value calculated from the differences measured using samples from these subjects).

In an embodiment, the corresponding sample used to determine the control variation value is a sample of the same type (e.g., the samples obtained before and after the application of a mechanical stimulus or force are plasma samples) as that from the subject. In an embodiment, the corresponding sample used to measure the second level of OPN of the subject is a sample of the same type (e.g., the samples obtained before and after the application of a mechanical stimulus or force are plasma samples) as that used to measure the first level of OPN from the subject.

In an embodiment, a lower or higher variation refers to a variation of at least about 10%, in further embodiments at least about 15%, 20%, 25%, 30%, 35%, 40%, 45%, 50%, 55%, 60%, 65%, 70% 75%, 80%, 85%, 90%, 95% 100% (2-fold), 150% or 200% between the variation in OPN levels obtained with the test/subject samples (samples obtained from the subject being tested) relative to the control variation value. In an embodiment, a substantially identical variation refers to a variation that differs by less than 10%, in further embodiments by less than 9%, 8%, 7%, 6%, 5% or less, as compared to the control variation value.

The changes in the levels of OPN may be detected at the nucleic acid or polypeptide levels using any methods known in the art for measuring nucleic acid or polypeptide levels (e.g., by detecting a nucleic acid or polypeptide comprising one of the sequences of FIG. 3). Non-limiting examples of methods for measuring nucleic acid levels include polymerase chain reaction (PCR), reverse transcriptase-PCR (RT-PCR) in situ PCR, SAGE, quantitative PCR (q-PCR), in situ hybridization, Southern blot, Northern blot, sequence analysis, microarray analysis, detection of a reporter gene, or other DNA/RNA hybridization platforms.

In an embodiment, OPN levels are measured at the polypeptide levels, e.g., by detecting a polypeptide comprising an amino acid sequence of FIG. 3. Non-limiting examples of methods for measuring polypeptide levels include Western blot, tissue microarray, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence-activated cell sorting (FACS), flow cytometry, and assays based on a property of the protein including but not limited to DNA binding, ligand binding, or interaction with other protein partners.

Antibodies specific for OPN ("anti-OPN antibodies"), which may be used to detect OPN in a biological sample in the methods of the present invention, are well known in the art and are commercially available from various providers such as Abcam™ (Cat. Nos. ab8448, ab14175, ab14176 and ab33046) and ABBIOTEC™ (Cat. No. 250801). Furthermore, Table I below provides a list of commercially available human OPN ELISA kits that may be used in the methods of the present invention.

TABLE I

Commercially available human OPN ELISA kits
COMMERCIALLY AVAILABLE OSTEOPONTIN DETECTION KITS

| Company | Kit Name | Catalogue Number | Sensitivity |
| --- | --- | --- | --- |
| IBL Hambourg | Human Osteopontin ELISA | JP 17158 | 3.33 ng/ml |
| IBL America | Human Osteopontin N-Half Assay Kit-IBL | 27258 | 3.90 pmol/L |
| IBL America | Human Osteopontin Assay Kit-IBL | 27158 | 3.33 ng/ml |
| Assay Designs | Osteopontin (human) EIA kit | 900-142 | 0.11 ng/ml |
| American Research Products Inc. | Osteopontin, human kit | 17158 | NA |
| R & D Systems | Human Osteopontin (OPN) ELISA Kit | DOST00 | 0.024 ng/ml |
| Promokine | Human Osteopontin ELISA | PK-EL-KA4231 | 3.6 ng/ml |
| USCNK Life Sciences Inc. | ELISA kit for human Osteopontin (OPN) | E90899HU | 0.14 ng/ml |
| BioVendor | Osteopontin (OPN) Human ELISA | BBT0482R | <50 pg/ml |

Both monoclonal and polyclonal antibodies directed to OPN may be used in the methods of the present invention.

Such antibodies may be produced by well established procedures known to those of skill in the art.

As used herein, the terms "anti-OPN antibody" or "immunologically specific anti-OPN antibody" refers to an antibody that specifically binds to (interacts with) an OPN protein (e.g., an OPN polypeptide having the sequence set forth in FIG. 6) and displays no substantial binding to other naturally occurring proteins other than the ones sharing the same antigenic determinants as the OPN protein.

The term antibody or immunoglobulin is used in the broadest sense, and covers monoclonal antibodies (including full length monoclonal antibodies), polyclonal antibodies, multispecific antibodies, antibody fragments (e.g., Fab and Fab' fragments), and antibody variants such as single-chain antibodies, humanized antibodies, chimeric antibodies so long as they exhibit the desired biological activity.

Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories).

Polyclonal antibodies are preferably raised in animals by multiple subcutaneous (sc), intravenous (iv) or intraperitoneal (ip) injections of the relevant antigen (e.g., a polypeptide having a sequence set forth in FIG. 6 or a fragment thereof) with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or $R^1N=C=NR$, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025, 155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In an embodiment, the methods are performed in a format suitable for high throughput assays, e.g., 96- or 384-well format, and suitable robots, (e.g., pipetting robots), and instrumentation may be used.

As used herein, mechanical stimulus or force refers to a stimulation of one or more members/body parts (e.g., finger(s), arm(s), thigh(s), leg(s), a combination of any of the foregoing, etc.) of the subject through mechanical means, for example using an apparatus/device such as an isokinetic machine, corset, vibrant plates or an inflatable strap (e.g., cuff for thighs or arms, ring, etc.), through physical exercise (e.g., standardized exercises) or through biomechanical stimulations by manipulation (e.g., massage). Examples of apparatus/devices suitable to induce a mechanical stimulus or force are known in the art and include air compression massage therapy devices, intermittent pneumatic compression devices, the Air compression therapy System™ (DL-2002D) and the DVT Prevention Device DVT2600 commercialized by Daesung Maref Co., Ltd.; the Petite Basic System commercialized by Mego Afek A C Ltd, as well as those described in US Patent Publication No. 20090177127, Galili et al., *Thromb Res.* 2007 121(1):37-41. Epub 2007 Apr. 17; Colwell et al., *J Bone Joint Surg Am.* 2010 92(3):527-35, U.S. Pat. Nos. 6,905,456 and 6,916,298. As used herein, one or more members is used interchangeably with one or more body parts. It refers e to one or more finger(s), arm(s), thigh(s), leg(s), a combination of any of the foregoing, etc.

In an embodiment, the above-mentioned mechanical stimuli or force is a pulsatile compressive pressure, in an embodiment a pulsatile compressive pressure of about 0-6 psi, in a further embodiment a pulsatile compressive pressure of about 0-4 psi. In a further embodiment, the above-mentioned pulsatile compressive pressure is applied using an inflatable cuff. In another embodiment, the above-mentioned mechanical force or stimuli is applied to one or both arms of the subject. In a further embodiment, the above-mentioned mechanical force or stimuli is applied to one arm of the subject and the biological sample (e.g. blood-derived sample) is collected/drawn from the opposite arm.

The above-mentioned mechanical force or stimulus may be applied for a period of time sufficient to induce an OPN response (e.g., to increase the levels of circulating OPN) in a subject. In the Examples presented below, the force or stimulus was applied on an arm for 30, 60 and 90 minutes. The 90 minute duration was selected as acceptable in a pediatric setting, other pediatric tests lasting up to that duration. This duration was therefore selected for practical reasons (e.g., parents and children may be more reluctant to undergo the test if it is much longer). It is believed however that the force or stimulus may be applied much longer than 90 minutes. The above-mentioned mechanical force or stimulus may be applied for example for a period of at least about 15 minutes, at least about 30 minutes, at least about 60 minutes or at least about 90 minutes. In an embodiment, the above-mentioned mechanical stimuli or force is applied for a period of between about 15 to about 200 minutes, in a further embodiment for a period of between about 30 to about 90 minutes, in a further embodiment for about 90 minutes. The arm was also selected as body part on which pressure would be applied for practical reasons (e.g., inflatable cuffs are common medical apparatus, parents and children are accustomed to this equipment, etc.). It was believed that larger equipments that could be used to apply pressure on the thighs for example could have increased anxiety of parents and children and reduced the number of participants. It is expected that applying pressure on a larger body surface may increase OPN level variation more rapidly and decrease the time delay required to perform the test.

Also provided by the present invention are kits for practicing the above-mentioned methods. The kits may include, for example, one or more reagent(s) to determine OPN levels in a sample, as well as buffers, containers, control samples (e.g., samples from a subject not having and not a likely candidate for developing scoliosis), etc. for performing the subject assays. The various components of the kit may be present in separate containers or certain compatible components may be pre-combined into a single container, as desired.

In addition to one or more of the above-mentioned components, the kits typically further include instructions for using the components of the kit to practice the methods (instructions for correlating the OPN levels with a diagnosis of a scoliosis and/or of a predisposition to developing a scoliosis). The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate. In addition to one or more of the above-mentioned components, the kits may further include a device for applying the mechanical stimulus or force (e.g., inflatable strap such as finger cuff, or inflatable cuff).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 6 presents the nucleotide sequences of the three human OPN isoforms (transcript variant 1, mRNA NM_001040058 (SEQ ID NO: 1); transcript variant 2, mRNA NM_000582 (SEQ ID NO: 2); transcript variant 3, mRNA NM_001040060 (SEQ ID NO: 3) and the amino acid sequences of the three human OPN isoforms (isoform a NP_001035147 (SEQ ID NO: 4); isoform b NP_000573 (SEQ ID NO: 5); and isoform c NP_001035149 (SEQ ID NO: 6)).

DESCRIPTION OF ILLUSTRATIVE EMBODIMENTS

The present invention is illustrated in further details by the following non-limiting examples.

Example 1

Materials and Methods

Figure 1:
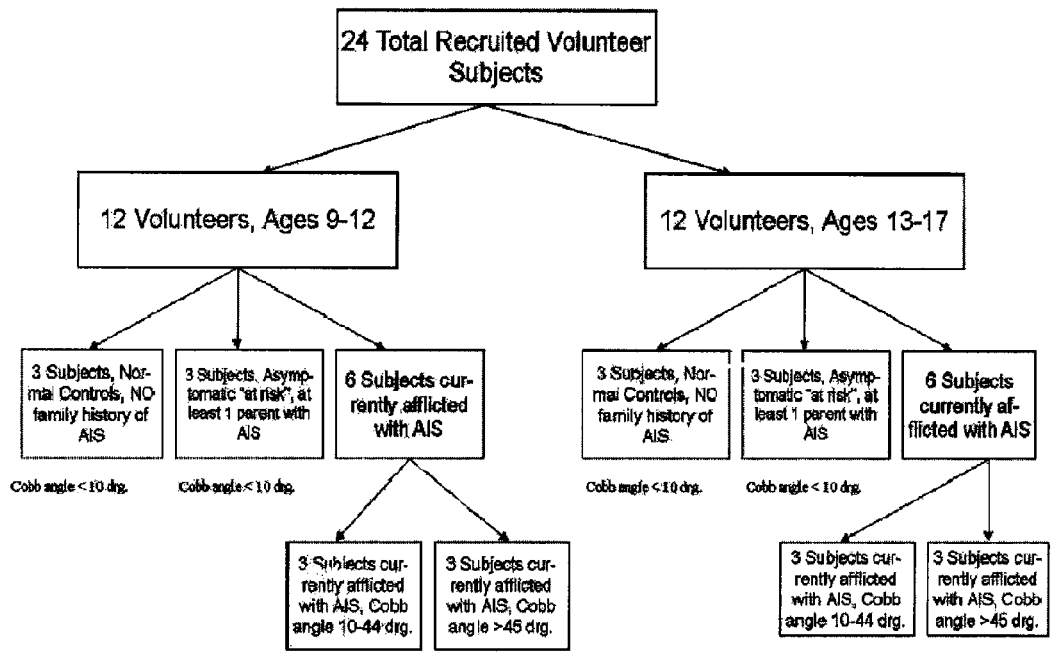
FIG. 1 shows an overview of the design of the experiments described herein.
Figure 1:
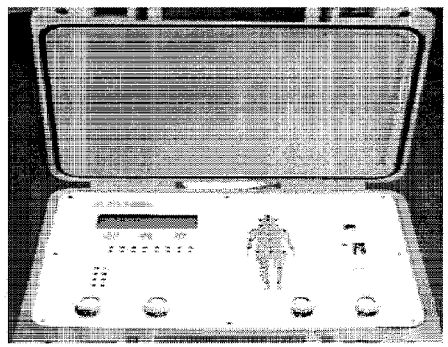

Twenty-one (21) test subjects between the ages of 9-17 were recruited, each of whom fall into one of 3 subject groups: i) surgical cases (pre-surgery, Cobb angle≥45° (n=3), ii) moderately affected cases (Cobb angle 10-44°) (n=12); and iii) healthy controls (n=6). The clinical characteristics of the recruited subjects are presented in Table II below. An overview of the experimental design is depicted in FIG. 1 and further described in more details in Example 3 below.

TABLE II

CLINICAL CHARACTERISTICS OF SUBJECTS RECRUITED BEFORE OCT. 4, 2010

| Patient Random ID | Characteristics | | |
|---|---|---|---|
| | Gender | Age (Years) | Clinical Group |
| 1679 | Female | 13 | AIS ≥45° |
| 1681 | Female | 13 | AIS ≥45° |
| 1680 | Female | 15 | AIS ≥45° |

TABLE II-continued

CLINICAL CHARACTERISTICS OF SUBJECTS
RECRUITED BEFORE OCT. 4, 2010

| Patient Random ID | Characteristics | | |
|---|---|---|---|
| | Gender | Age (Years) | Clinical Group |
| 827 | Female | 9 | AIS 10-44° |
| 793 | Female | 10 | AIS 10-44° |
| 844 | Female | 10 | AIS 10-44° |
| 832 | Male | 11 | AIS 10-44° |
| 865 | Female | 11 | AIS 10-44° |
| 853 | Female | 11 | AIS 10-44° |
| 850 | Female | 14 | AIS 10-44° |
| 847 | Female | 15 | AIS 10-44° |
| 785 | Male | 16 | AIS 10-44° |
| 851 | Female | 16 | AIS 10-44° |
| 864 | Female | 16 | AIS 10-44° |
| 849 | Male | 17 | AIS 10-44° |
| 4211 | Female | 10 | Healthy Control Subjects |
| 4282 | Male | 12 | Healthy Control Subjects |
| 4283 | Male | 15 | Healthy Control Subjects |
| 4213 | Male | 15 | Healthy Control Subjects |
| 4000A | Male | 9 | Healthy Control Subjects |
| 4000B | Male | 15 | Healthy Control Subjects |

An initial blood sample was taken from the subjects to establish a baseline value of circulating OPN. One of the arms from each subject was then wrapped with an inflatable cuff from an Advanced Biomechanical Rehabilitation (ABR) therapeutic Massager™, which applied a dynamic, pulsatile, compressive pressure of variable amplitude from 0-4 psi at 0.006 Hz to the arm for a period of 90 minutes. At intervals of 30 minutes after the start of force application, additional blood samples were taken in order to monitor circulating OPN levels in subjects. OPN levels were measured using the Human Osteopontin ELISA kit from IBL (Hambourg), Cat. No. JP 17158.

Using the software suite R, significance of OPN changes vs. subject Cobb angle was first fit to a linear mathematical model. Then, the ANOVA test was performed to analyze the significance of relationship between OPN changes versus patient Cobb angle group or healthy control subjects. As generally recommended by the literature, as a final step a TukeyHSD (post-hoc) test was performed to perform a multiple comparison of means (with 95% confidence intervals) pairwise between Cobb angle groups and healthy control group.

Example 2

Results

Figure 2:
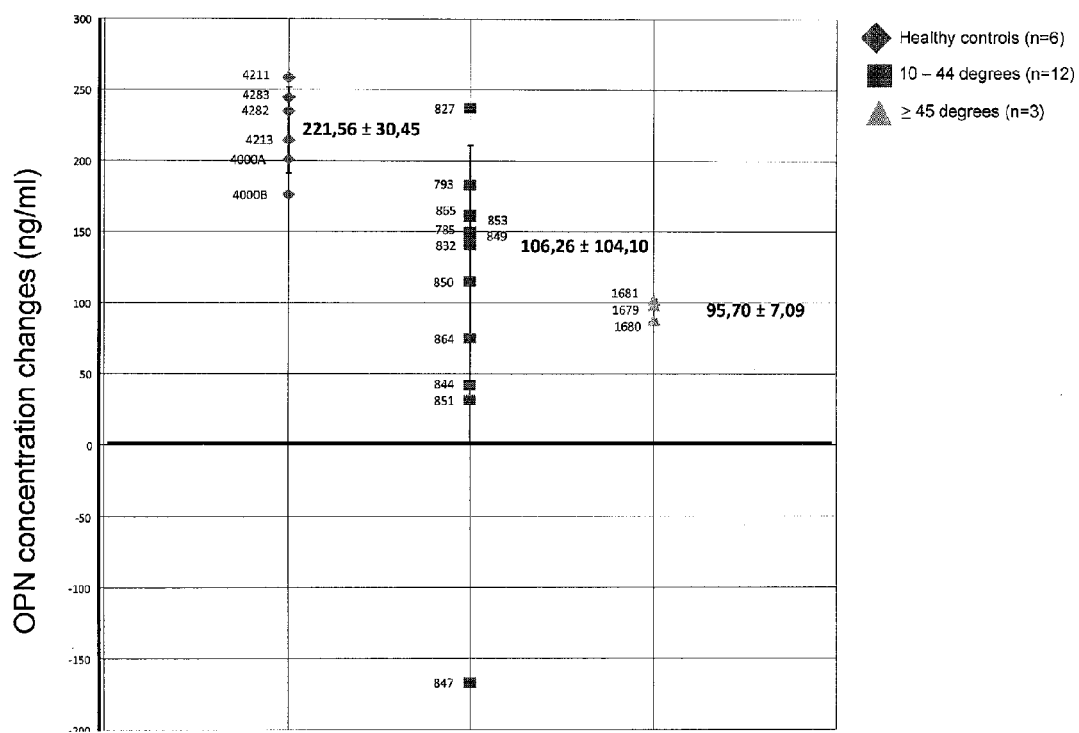
FIG. 2 shows the changes in OPN levels in control subjects (diamonds, left), moderately affected scoliosis patients (squares, middle) and surgical case subjects (triangles. right) after 90 minutes of periodic compressive mechanical stimulation, 0-4 psi, 0.006 Hz.

As shown in FIG. 2, OPN responses can be provoked in vivo by bodily-applied mechanical force. A >2-fold difference ($p=0.002082$) was detected in the provoked OPN response of the control patient group average (n=6) vs. that of the surgical case group (n=3) after 90 minutes. In addition, the moderately affected group (n=12) response average was also lower as compared to that of the controls.

Example 3

Materials and Methods

Study Population

The internal review board of CHU Sainte-Justine approved the study. Parents or legal guardians of all study participants gave their informed written consent, and minors their assent. Subjects were recruited from among the general patient population of the orthopaedic clinic of Sainte-Justine.

Between January 2010 and March 2011, a total of 38 subjects (mean age 13.69±2.25) of various ethnicities were recruited including the 21 subjects listed in Table II above. Four particular classes of patients aged 9-17 were sought: i) controls (mean age 13.87±2.41) (n=10); ii) asymptomatic "at risk" subjects (n=7) (mean age 13.16±2.78); iii) moderately affected (Cobb angle 10-44°) (mean age 13.43±2.50) (n=13); and iv) severely affected individuals (Cobb angle≥45°) (mean age 14.26±1.27) (n=9).

A person was deemed to be affected if history and physical examination were consistent with the diagnosis of idiopathic scoliosis and a minimum of a ten degree curvature in the coronal plane with vertebral rotation was found on radiograph. The Cobb angle as measured on the radiograph then determined a patient's status as either moderately or severely affected. Asymptomatic at-risk children were recruited and examined in a special early screening clinic, defined as those with less than a 10 degree curvature but with a family history of AIS. Controls did not have any family history of AIS, and a less than 10 degree spinal curvature. Subject exclusion criteria from data analysis included: i) regular utilization of contraceptive drugs; ii) BMI greater than 35; iii) employment of any external physical apparatus to help stabilize the spinal cord. Patient and control subjects clinical data are summarized in Table III below.

TABLE III

CLINICAL CHARACTERISTICS OF SUBJECTS
RECRUITED BEFORE SEP. 22, 2011

| | Experimental Group | Age at Time of Testing | Gender | Curve Type | Cobb Angle |
|---|---|---|---|---|---|
| 1 | >45° | 12.6 | F | lTrTlL | 30-71-34 |
| 2 | >45° | 13.8 | F | | |
| 3 | >45° | 13.6 | F | | |
| 4 | >45° | 13.6 | F | rTlL | 57-44 |
| 5 | >45° | 13.8 | F | ITL | 54 |
| 6 | >45° | 13.7 | F | lTrTlL | 32-51-24 |
| 7 | >45° | 15.3 | F | | |
| 8 | >45° | 15 | F | | |
| 9 | >45° | 16.9 | M | rTlTL | 39-59 |
| 10 | 10-44° | 9.5 | F | rT | 11 |
| 11 | 10-44° | 10.9 | F | rTlL | 36-40 |
| 12 | 10-44° | 12 | F | rT | 16 |
| 13 | 10-44° | 11.7 | F | lTrT | 23-25 |
| 14 | 10-44° | 11 | F | ITL | 11 |
| 15 | 10-44° | 11.6 | M | rTlL | 18-14 |
| 16 | 10-44° | 13.7 | F | ITL | 16 |
| 17 | 10-44° | 13.8 | F | rTlTL | 43-24 |
| 18 | 10-44° | 14.7 | F | ITL | 16 |
| 19 | 10-44° | 16.3 | F | rTlL | 16-16 |
| 20 | 10-44° | 16.3 | M | | |
| 21 | 10-44° | 16.2 | M | rTL | 35 |
| 22 | 10-44° | 17 | M | rTlL | 21-30 |
| 23 | Asymptomatic | 9.4 | M | ITL | 12 |
| 24 | Asymptomatic | 10.8 | F | rTlL | 5-6' |
| 25 | Asymptomatic | 11.5 | M | N/A | 0 |
| 26 | Asymptomatic | 12.8 | F | rTlTL | 8-8 |
| 27 | Asymptomatic | 15.2 | F | rTlL | 4-4 |
| 28 | Asymptomatic | 15.4 | M | rL | 6 |
| 29 | Asymptomatic | 17 | F | N/A | N/A |
| 30 | CTRL | 10.8 | F | N/A | N/A |
| 31 | CTRL | 12.8 | M | N/A | N/A |
| 32 | CTRL | 13 | F | N/A | N/A |
| 33 | CTRL | 15 | F | N/A | N/A |
| 34 | CTRL | 15.7 | M | N/A | N/A |
| 35 | CTRL | 15.9 | M | N/A | N/A |
| 36 | CTRL | 15.5 | M | N/A | N/A |

TABLE III-continued

CLINICAL CHARACTERISTICS OF SUBJECTS
RECRUITED BEFORE SEP. 22, 2011

| | Experimental Group | Age at Time of Testing | Gender | Curve Type | Cobb Angle |
|---|---|---|---|---|---|
| 37 | CTRL | 16 | F | N/A | N/A |
| 38 | CTRL | 9 | M | N/A | N/A |
| 39 | CTRL | 15 | M | N/A | N/A |

Curve type code: r = right; l = left; T = thoracic; L = lumbar; TL = thoracolumbar; N/A = not available. 9 severely affected (mean age 14.26 ± 1.27), 13 moderately affected (mean age 13.43 ± 2.50), 7 asymptomatics (mean age 13.16 ± 2.78), and 10 control subjects (mean age 13.87 ± 2.41).

Mechanical Force Stimulation

Upon arrival, participants in the study were asked to lie flat on a hospital bed. After allowing the patient to settle and rest on the bed for 5-10 minutes, an initial blood sample was drawn from one of the arms of the patient.

Subsequently, a pair of medium-sized air bladders from an Advanced Biomechanical Rehabilitation (ABR) therapeutic air massager device (Panacis Medical, Ottawa, Ontario) were arranged and attached to the other arm, in much the same manner as one would a sphygmomanometer, as described in the product documentation. This ABR device has been certified by numerous health and regulatory agencies in North America, the EU, and around the world, including a Health Canada authorization for clinical use on patients. The massager device was reprogrammed from the manufacturer's preset settings in order to produce cycles of inflation/deflation of the bladders at a frequency of approximately 0.006 Hz, supplying a pulsatile compressive stress ranging from 0-4 psi to the area of the arm covered by the medium-sized air bladders. Patients experienced the stimulation for a total of 90 minutes, during which time blood samples from the non-stimulated arm were taken, every thirty minutes, making a total of four blood samples (roughly 5-6 ml each) drawn per patient, including the initial at t=0 min.

OPN and sCD44 Enzyme-Linked Immunosorbent Assays

Blood samples from AIS patients, asymptomatic at-risk children and healthy control subjects were obtained in order to determine plasma levels of OPN and sCD44. They were collected in EDTA-treated tubes and then centrifuged. Derived plasma samples were aliquoted and kept frozen at −80° C. until thawed and analyzed. Plasma concentrations of OPN and sCD44std (standard isoform) were measured by capture enzyme-linked immunosorbent assays (ELISA) according to protocols provided by the manufacturer (IBL, Hamburg, Germany). The OPN ELISA kit measures total concentration of both phosphorylated and non-phosphorylated forms of OPN in plasma whereas the sCD44std ELISA kit detects all circulating CD44 isoforms. All ELISA tests were performed in duplicate and the optical density was measured at 450 nm using an AsysHiTech™ Expert-96 microplate reader (Biochrom, Cambridge, UK).

Statistical Analysis

Average group levels of OPN and sCD44 are presented as mean±SD. Statistical significance p-values of differences in group levels of OPN and sCD44 between control, asymptomatic, moderately affected, and severely affected patients was respectively assessed in the first instance using linear regression models with a one-way ANOVA. The effects of age and gender were then individually studied, each in combination with grouping, using a two-way ANOVA with weighted means and Type I sums of squares to account for unbalanced sample sizes (i.e. age and group, followed by gender and group as factors in the analyses), where age groups for ANOVA analyses were defined as younger subjects between 9-12 years of age and those between 13-17 years. Patient environmental factors were compared across experimental groups with Fisher's exact test for discrete variables and again post-hoc for any factors identified as significant, and a one-way ANOVA for continuous variables (average age in each group). P-values<0.05 were considered statistically significant. The software used for all statistical computations was R, version 2.13.1 (Team, R.D.C., R: A language and environment for statistical computing, version 2.13. 1, 2011, R Foundation for Statistical Computing Vienna: Vienna, Austria.).

Example 4

Results

Circulating OPN and sCD44 Levels

Figure 3:
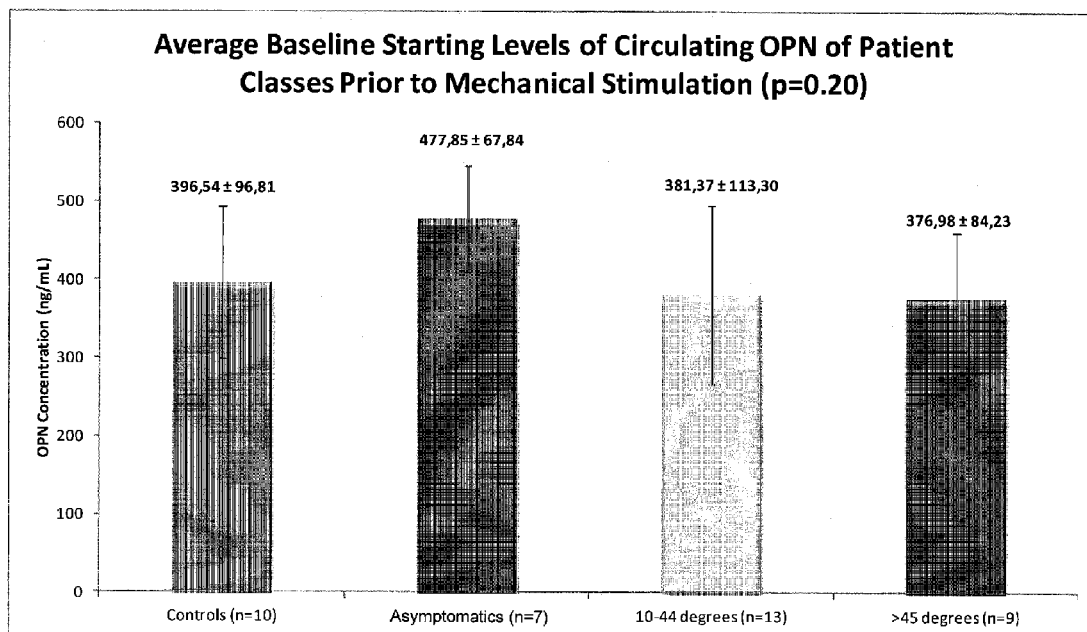
FIG. 3 shows the average initial circulating OPN levels (mean±SD) among experimental subgroups prior to mechanical stimulation. No significant difference was found between groups (p=0.20, one-way ANOVA)
Figure 4:
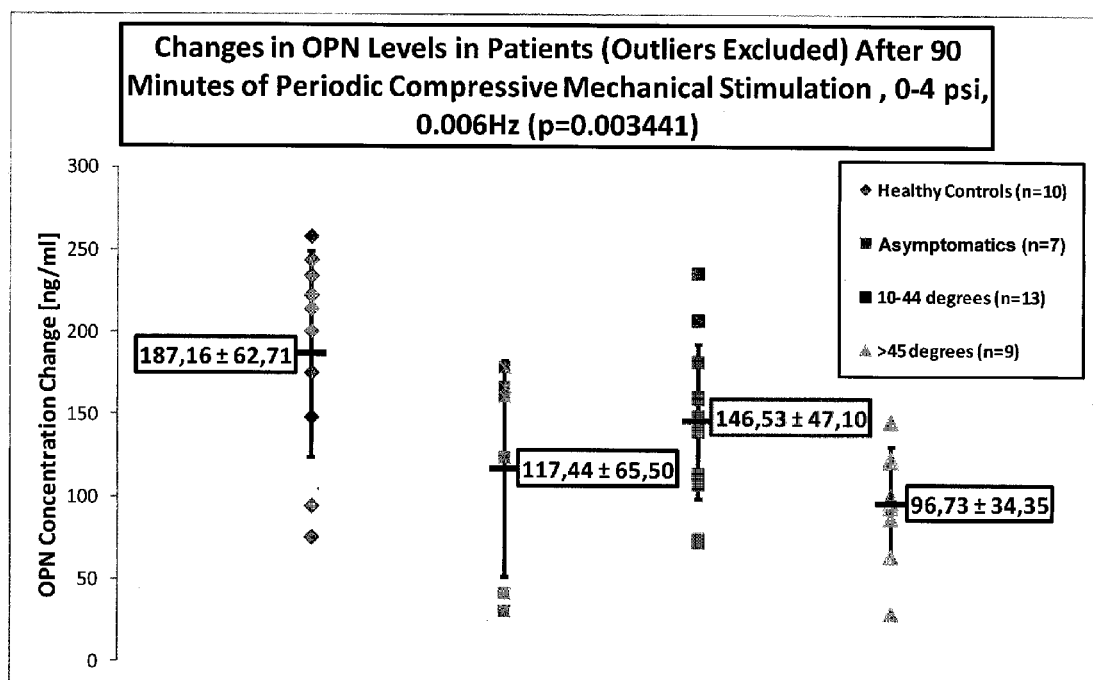
FIG. 4 shows the average change in OPN levels (mean±SD) among experimental subgroups after 90 minutes of mechanical stimulation. A strongly significant difference was found between groups (p=0.003441, one-way ANOVA)

Initial starting values of circulating OPN levels in blood were not found to be significantly different between experimental groups (one-way ANOVA p=0.20), as shown in FIG. 3. Average circulating OPN levels of all 4 experimental groups increased over the course of the 90 minutes of mechanical stimulation. A raw box plot of subject OPN level variation by experimental group is shown in FIG. 4. Interestingly, there was a trend found, that patient grouping and OPN level variation were strongly significantly correlated (one-way ANOVA p=0.003441), with average group OPN level variation declining as the group curve severity increased. Tukey's HSD post-hoc test showed that there was very statistically significant variation between the severely affected group and the control (p=0.0029), but not between other pairwise group combinations, though there was borderline significant correlation suggested between moderately and severely affected groups (p=0.084) as well as between the control and asymptomatic groups (p=0.0593). A relative homogeneity was observed within each experimental group in terms of the OPN level variation, as evidenced by the reasonable standard deviations in each, and the absence of any particularly gross outliers.

Figure 5:
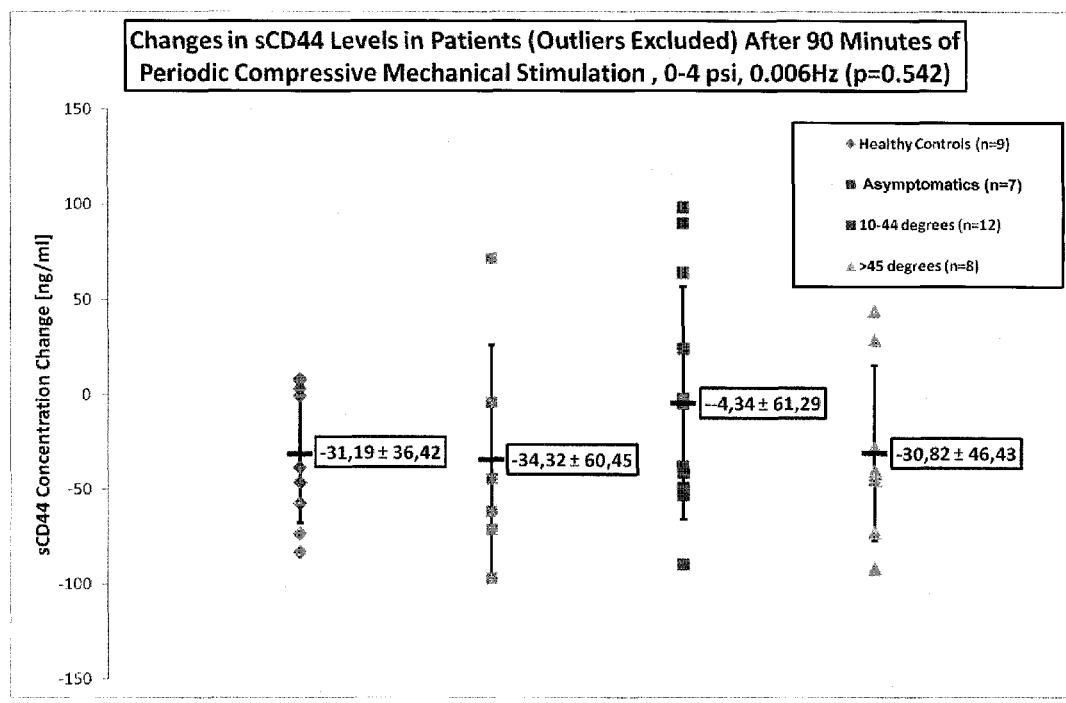
FIG. 5 shows the average change in sCD44 levels (mean±SD) among experimental subgroups after 90 minutes of mechanical stimulation. No significant difference was found between groups (p=0.542, one-way ANOVA)

No statistically significant correlation was observed between patient grouping and sCD44 level variation (p=0.542), as shown in FIG. 5.

Effects of Age and Gender

To study whether OPN level variation (ΔOPN) was affected by the age and sex of subjects, two-way ANOVA analyses with unbalanced sample sizes were carried-out and Type I sums of squares, first with gender and experimental group as factors. Using this model construct, it was found that gender had a statistically significant effect on ΔOPN, in conjunction with experimental group (gender p=0.004664, experimental group p=0.002664, with gender as the first factor). The data was then analyzed with the factor order reversed, and found that gender still had a statistically significant effect on ΔOPN, in conjunction with experimental group (gender p=0.0215275, experimental group p=0.0009763, with experimental group as the first factor). A statistically significant interaction was found between gender and experimental group (interaction p=0.028523). By contrast, age grouping was statistically significant, in conjunction with experimental group, when age group was considered as the first factor (age group p=0.028624, experimental group p=0.006385), but only borderline statistically significant when considered as the second (age group p=0.052138, experimental group p=0.004397), with no significant interaction between the two factors (interaction p=0.793477).

Although the present invention has been described hereinabove by way of specific embodiments thereof, it can be modified, without departing from the spirit and nature of the subject invention as defined in the appended claims.

The invention claimed is:

1. A method for stratifying a subject having a scoliosis or at risk of developing a scoliosis, said method comprising:
   (a) measuring a first level of circulating osteopontin (OPN) protein in a plasma sample from said subject;
   (b) applying a pulsatile compressive pressure to one or more members from said subject for a time sufficient to increase circulating OPN protein level in corresponding control plasma samples from subjects not having a scoliosis or not at risk of developing a scoliosis;
   (c) measuring a second level of circulating OPN protein in a corresponding plasma sample from said subject after the application of said pulsatile compressive pressure in step (b);
   (d) determining a variation between said first level of circulating OPN protein and said second level of circulating OPN protein,
   wherein said variation is an increase in circulating OPN level following the application of said pulsatile compressive pressure;
   (e) comparing said variation to a control variation value, wherein said control variation value corresponds to a variation between a first level of circulating OPN protein and a second level of circulating OPN protein determined in corresponding plasma samples from subjects not having a scoliosis or not at risk of developing a scoliosis; and
   (f) (i) stratifying said subject in a first group when said variation is lower in said sample as compared to said control variation value; or
       (ii) stratifying said subject in a second group when said variation is equal or higher in said sample as compared to said control variation value,
   wherein said measuring comprises:
       (1) contacting said sample with an antibody specific for said OPN protein; and
       (2) immunodetecting the level of circulating OPN protein in said sample.

2. The method of claim 1, wherein stratifying said subject in said first group identifies said subject as being at risk of developing a scoliosis.

3. The method of claim 1, wherein said scoliosis is an idiopathic scoliosis.

4. The method of claim 3, wherein said idiopathic scoliosis is adolescent idiopathic scoliosis (AIS).

5. The method of claim 4, wherein said one or more members is an arm.

6. The method of claim 4, wherein said pulsatile compressive pressure is applied using an inflatable strap.

7. The method of claim 4, wherein said pulsatile compressive pressure is applied using an inflatable cuff.

8. The method of claim 4, wherein said pulsatile compressive pressure is applied for a period of at least about 15 minutes.

9. The method of claim 4, wherein said pulsatile compressive pressure is applied for a period of between about 30 to about 90 minutes.

10. The method of claim 4, wherein said pulsatile compressive pressure is applied for a period of about 90 minutes.

11. The method of claim 4, wherein the subject is a subject at risk of developing AIS.

12. The method of claim 4, further comprising stratifying said subject of the first group in a first subgroup when said variation is less than about twofold lower than said control variation value and in a second subgroup when said variation is at least about twofold lower than said control variation value.

13. The method of claim 4, wherein said lower variation in step (f) (i) is less than about twofold lower than said control variation value.

14. A method for stratifying a subject having a scoliosis or at risk of developing a scoliosis, said method comprising:
    (a) measuring a first level of circulating osteopontin (OPN) protein in a plasma sample from said subject;
    (b) applying a pulsatile compressive pressure to one or more members from said subject for a time sufficient to increase circulating OPN protein level in corresponding control plasma samples from subjects not having a scoliosis or not at risk of developing a scoliosis;
    (c) measuring a second level of circulating OPN protein in a corresponding plasma sample from said subject after the application of said pulsatile compressive pressure in step (b);
    (d) determining a variation between said first level of circulating OPN protein and said second level of circulating OPN protein,
    wherein said variation is an increase in OPN level following the application of said pulsatile compressive pressure;
    (e) comparing said variation to a first control variation value and a second control variation value,
    wherein said first control variation value corresponds to a variation between a first level of circulating OPN protein and a second level of circulating OPN protein determined in corresponding plasma samples from subjects not having a scoliosis or not at risk of developing a scoliosis; and
    wherein said second control variation value corresponds to a variation between a first level of circulating OPN protein and a second level of circulating OPN protein determined in corresponding plasma samples from subjects having a scoliosis with a Cobb angle above 45°; and
    (f) (i) stratifying said subject in a first group when said variation is lower in said sample as compared to said first control variation value and higher in said sample as compared to said second control variation value;
        (ii) stratifying said subject in a second group when said variation is about equal or lower in said sample as compared to said second control variation value; or
        (iii) stratifying said subject in a third group when said variation is about equal or higher in said sample as compared to said first control variation value,
    wherein said measuring comprises;
        (1) contacting said sample with an antibody specific for said OPN protein; and
        (2) immunodetecting the level of circulating OPN in said sample.

15. The method of claim 14, wherein stratifying said subject in said first group identifies said subject as at risk of developing a scoliosis.

16. The method of claim 14, wherein said scoliosis is idiopathic scoliosis (IS).

17. The method of claim 16, wherein said idiopathic scoliosis is adolescent idiopathic scoliosis (AIS).

18. The method of claim 17, wherein said one or more members is an arm.

19. The method of claim 17, wherein said pulsatile compressive pressure is applied using an inflatable strap.

20. The method of claim 17, wherein said pulsatile compressive pressure is applied using an inflatable cuff.

21. The method of claim 17, wherein said pulsatile compressive pressure is applied for a period of at least about 15 minutes.

22. The method of claim 17, wherein said pulsatile compressive pressure is applied for a period of between about 30 to about 90 minutes.

23. The method of claim 17, wherein said pulsatile compressive pressure is applied for a period of about 90 minutes.

24. The method of claim 17, wherein the subject is a likely candidate for developing adolescent idiopathic scoliosis.

* * * * *

SEQUENCE LISTING

<160> NUMBER OF SEQ ID NOS: 6

<210> SEQ ID NO 1
<211> LENGTH: 1641
<212> TYPE: DNA
<213> ORGANISM: homo sapiens

<400> SEQUENCE: 1

| ctccctgtgt tggtggagga tgtctgcagc agcatttaaa ttctgggagg gcttggttgt | 60 |
| cagcagcagc aggaggaggc agagcacagc atcgtcggga ccagactcgt ctcaggccag | 120 |
| ttgcagcctt ctcagccaaa cgccgaccaa ggaaaactca ctaccatgag aattgcagtg | 180 |
| atttgctttt gcctcctagg catcacctgt gccataccag ttaaacaggc tgattctgga | 240 |
| agttctgagg aaaagcagct ttacaacaaa tacccagatg ctgtggccac atggctaaac | 300 |
| cctgacccat ctcagaagca gaatctccta gccccacaga atgctgtgtc ctctgaagaa | 360 |
| accaatgact ttaaacaaga gacccttcca agtaagtcca cgaaagcca tgaccacatg | 420 |
| gatgatatgg atgatgaaga tgatgatgac catgtggaca gccaggactc cattgactcg | 480 |
| aacgactctg atgatgtaga tgacactgat gattctcacc agtctgatga gtctcaccat | 540 |
| tctgatgaat ctgatgaact ggtcactgat tttcccacgg acctgccagc aaccgaagtt | 600 |
| ttcactccag ttgtccccac agtagacaca tatgatggcc gaggtgatag tgtggtttat | 660 |
| ggactgaggt caaaatctaa gaagtttcgc agacctgaca tccagtaccc tgatgctaca | 720 |
| gacgaggaca tcacctcaca catggaaagc gaggagttga atggtgcata caaggccatc | 780 |
| cccgttgccc aggacctgaa cgcgccttct gattgggaca gccgtgggaa ggacagttat | 840 |
| gaaacgagtc agctggatga ccagagtgct gaaacccaca gccacaagca gtccagatta | 900 |
| tataagcgga agccaatga tgagagcaat gagcattccg atgtgattga tagtcaggaa | 960 |
| ctttccaaag tcagccgtga attccacagc catgaatttc acagccatga agatatgctg | 1020 |
| gttgtagacc ccaaaagtaa ggaagaagat aaacacctga aatttcgtat ttctcatgaa | 1080 |
| ttagatagtg catcttctga ggtcaattaa aaggagaaaa aatacaattt ctcactttgc | 1140 |
| atttagtcaa aagaaaaaat gctttatagc aaaatgaaag agaacatgaa atgcttcttt | 1200 |
| ctcagtttat tggttgaatg tgtatctatt tgagtctgga ataactaat gtgtttgata | 1260 |
| attagtttag tttgtggctt catggaaact ccctgtaaac taaaagcttc agggttatgt | 1320 |
| ctatgttcat tctatagaag aaatgcaaac tatcactgta ttttaatatt tgttattctc | 1380 |
| tcatgaatag aaatttatgt agaagcaaac aaaatacttt tacccactta aaaagagaat | 1440 |
| ataacatttt atgtcactat aatctttgt tttttaagtt agtgtatatt ttgttgtgat | 1500 |
| tatcttttg tggtgtgaat aaatcttta tcttgaatgt aataagaatt tggtggtgtc | 1560 |
| aattgcttat ttgttttccc acggttgtcc agcaattaat aaaacataac ctttttact | 1620 |
| gcctaaaaaa aaaaaaaaa a | 1641 |

<210> SEQ ID NO 2
<211> LENGTH: 1616
<212> TYPE: DNA
<213> ORGANISM: homo sapiens

<400> SEQUENCE: 2

| ctccctgtgt tggtggagga tgtctgcagc agcatttaaa ttctgggagg gcttggttgt | 60 |
| cagcagcagc aggaggaggc agagcacagc atcgtcggga ccagactcgt ctcaggccag | 120 |
| ttgcagcctt ctcagccaaa cgccgaccaa ggaaaactca ctaccatgag aattgcagtg | 180 |

```
atttgctttt gcctcctagg catcacctgt gccataccag ttaaacaggc tgattctgga    240
agttctgagg aaaagcagct ttacaacaaa tacccagatg ctgtggccac atggctaaac    300
cctgacccat ctcagaagca gaatctccta gccccacaga cccttccaag taagtccaac    360
gaaagccatg accacatgga tgatatggat gatgaagatg atgatgacca tgtggacagc    420
caggactcca ttgactcgaa cgactctgat gatgtagatg acactgatga ttctcaccag    480
tctgatgagt ctcaccattc tgatgaatct gatgaactgg tcactgattt tcccacggac    540
ctgccagcaa ccgaagtttt cactccagtt gtccccacag tagacacata tgatggccga    600
ggtgatagtg tggtttatgg actgaggtca aaatctaaga agtttcgcag acctgacatc    660
cagtaccctg atgctacaga cgaggacatc acctcacaca tggaaagcga ggagttgaat    720
ggtgcataca aggccatccc cgttgcccag gacctgaacg cgccttctga ttgggacagc    780
cgtgggaagg acagttatga aacgagtcag ctggatgacc agagtgctga aaccccacagc   840 cacaagcagt ccagattata taagcggaaa gccaatgatg agagcaatga gcattccgat    900
gtgattgata gtcaggaact tccaaagtc agccgtgaat tccacagcca tgaatttcac     960
agccatgaag atatgctggt tgtagacccc aaaagtaagg aagaagataa acacctgaaa    1020
tttcgtattt ctcatgaatt agatagtgca tcttctgagg tcaattaaaa ggagaaaaaa    1080
tacaatttct cactttgcat ttagtcaaaa gaaaaaatgc tttatagcaa aatgaaagag    1140
aacatgaaat gcttctttct cagtttattg gttgaatgtg tatctatttg agtctggaaa    1200
taactaatgt gtttgataat tagtttagtt tgtggcttca tggaaactcc ctgtaaacta    1260
aaagcttcag ggttatgtct atgttcattc tatagaagaa atgcaaacta tcactgtatt    1320
ttaatatttg ttattctctc atgaataaa atttatgtag aagcaaacaa atactttta     1380 cccacttaaa aagagaatat aacattttat gtcactataa tcttttgttt tttaagttag    1440
tgtatatttt gttgtgatta tcttttttgtg gtgtgaataa atcttttatc ttgaatgtaa    1500
taagaatttg gtggtgtcaa ttgcttattt gtttccccac ggttgtccag caattaataa    1560 aacataaacct tttttactgc ctaaaaaaaa aaaaaaaaaa aaaaaaaaaa aaaaaa       1616
```

<210> SEQ ID NO 3
<211> LENGTH: 1560
<212> TYPE: DNA
<213> ORGANISM: homo sapiens

<400> SEQUENCE: 3

```
ctccctgtgt tggtggagga tgtctgcagc agcatttaaa ttctgggagg gcttggttgt     60
cagcagcagc aggaggaggc agagcacagc atcgtcggga ccagactcgt ctcaggccag    120
ttgcagcctt ctcagccaaa cgccgaccaa ggaaaactca ctaccatgag aattgcagtg    180
atttgctttt gcctcctagg catcacctgt gccataccag ttaaacaggc tgattctgga    240
agttctgagg aaaagcagaa tgctgtgtcc tctgaagaaa ccaatgactt taaacaagag    300
acccttccaa gtaagtccaa cgaaagccat gaccacatgg atgatatgga tgatgaagat    360
gatgatgacc atgtggacag ccaggactcc attgactcga cgactctga tgatgtagat    420 gacactgatg attctcacca gtctgatgag tctcaccatt ctgatgaatc tgatgaactg    480
gtcactgatt tccccacgga cctgccagca accgaagttt tcactccagt tgtccccaca    540
gtagacacat atgatggccg aggtgatagt gtggtttatg gactgaggtc aaaatctaag    600
aagtttcgca gacctgacat ccagtaccct gatgctacag acgaggacat cacctcacac    660
```

```
atggaaagcg aggagttgaa tggtgcatac aaggccatcc ccgttgccca ggacctgaac    720
gcgccttctg attgggacag ccgtgggaag gacagttatg aaacgagtca gctggatgac    780
cagagtgctg aaacccacag ccacaagcag tccagattat ataagcggaa agccaatgat    840
gagagcaatg agcattccga tgtgattgat agtcaggaac tttccaaagt cagccgtgaa    900
ttccacagcc atgaatttca cagccatgaa gatatgctgg ttgtagaccc caaaagtaag    960
gaagaagata acaccctgaa atttcgtatt tctcatgaat tagatagtgc atcttctgag   1020
gtcaattaaa aggagaaaaa atacaatttc tcactttgca tttagtcaaa agaaaaaatg   1080
ctttatagca aaatgaaaga gaacatgaaa tgcttctttc tcagtttatt ggttgaatgt   1140
gtatctattt gagtctggaa ataactaatg tgtttgataa ttagtttagt ttgtggcttc   1200
atggaaactc cctgtaaact aaaagcttca gggttatgtc tatgttcatt ctatagaaga   1260
aatgcaaact atcactgtat tttaatattt gttattctct catgaataga aatttatgta   1320
gaagcaaaca aaatactttt acccacttaa aaagagaata taacatttta tgtcactata   1380
atcttttgtt tttaagtta gtgtatattt tgttgtgatt atcttttgt ggtgtgaata   1440
aatcttttat cttgaatgta ataagaattt ggtggtgtca attgcttatt tgttttccca   1500
cggttgtcca gcaattaata aaacataacc ttttttactg cctaaaaaaa aaaaaaaaa   1560
```

<210> SEQ ID NO 4
<211> LENGTH: 314
<212> TYPE: PRT
<213> ORGANISM: homo sapiens

<400> SEQUENCE: 4

```
Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220
```

```
Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
                260                 265                 270

Phe His Ser His Glu Phe His Ser His Glu Asp Met Leu Val Val Asp
                275                 280                 285

Pro Lys Ser Lys Glu Glu Asp Lys His Leu Lys Phe Arg Ile Ser His
                290                 295                 300

Glu Leu Asp Ser Ala Ser Ser Glu Val Asn
305                 310

<210> SEQ ID NO 5
<211> LENGTH: 300
<212> TYPE: PRT
<213> ORGANISM: homo sapiens

<400> SEQUENCE: 5

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
                35                  40                  45

Ser Gln Lys Gln Asn Leu Leu Ala Pro Gln Thr Leu Pro Ser Lys Ser
        50                  55                  60

Asn Glu Ser His Asp His Met Asp Asp Met Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
                100                 105                 110

Asp Glu Ser Asp Glu Leu Val Thr Asp Phe Pro Thr Asp Leu Pro Ala
                115                 120                 125

Thr Glu Val Phe Thr Pro Val Val Pro Thr Val Asp Thr Tyr Asp Gly
                130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
                180                 185                 190

Val Ala Gln Asp Leu Asn Ala Pro Ser Asp Trp Asp Ser Arg Gly Lys
                195                 200                 205

Asp Ser Tyr Glu Thr Ser Gln Leu Asp Asp Gln Ser Ala Glu Thr His
                210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
                260                 265                 270

Val Asp Pro Lys Ser Lys Glu Glu Asp Lys His Leu Lys Phe Arg Ile
```

```
                275                 280                 285

Ser His Glu Leu Asp Ser Ala Ser Ser Glu Val Asn
        290                 295                 300

<210> SEQ ID NO 6
<211> LENGTH: 287
<212> TYPE: PRT
<213> ORGANISM: homo sapiens

<400> SEQUENCE: 6

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
            20                  25                  30

Ala Val Ser Ser Glu Glu Thr Asn Asp Phe Lys Gln Glu Thr Leu Pro
        35                  40                  45

Ser Lys Ser Asn Glu Ser His Asp His Met Asp Asp Met Asp Asp Glu
    50                  55                  60

Asp Asp Asp Asp His Val Asp Ser Gln Asp Ser Ile Asp Ser Asn Asp
65                  70                  75                  80

Ser Asp Asp Val Asp Thr Asp Asp Ser His Gln Ser Asp Glu Ser
            85                  90                  95

His His Ser Asp Glu Ser Asp Glu Leu Val Thr Asp Phe Pro Thr Asp
            100                 105                 110

Leu Pro Ala Thr Glu Val Phe Thr Pro Val Val Pro Thr Val Asp Thr
        115                 120                 125

Tyr Asp Gly Arg Gly Asp Ser Val Val Tyr Gly Leu Arg Ser Lys Ser
    130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
            165                 170                 175

Ala Ile Pro Val Ala Gln Asp Leu Asn Ala Pro Ser Asp Trp Asp Ser
        180                 185                 190

Arg Gly Lys Asp Ser Tyr Glu Thr Ser Gln Leu Asp Asp Gln Ser Ala
    195                 200                 205

Glu Thr His Ser His Lys Gln Ser Arg Leu Tyr Lys Arg Lys Ala Asn
    210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
            245                 250                 255

Met Leu Val Val Asp Pro Lys Ser Lys Glu Glu Asp Lys His Leu Lys
        260                 265                 270

Phe Arg Ile Ser His Glu Leu Asp Ser Ala Ser Ser Glu Val Asn
    275                 280                 285
```